United States Patent [19]

Sakai et al.

[11] Patent Number: 4,927,767
[45] Date of Patent: May 22, 1990

[54] METHOD FOR THE DETECTION OF DISEASES ASSOCIATED WITH THE METABOLIC ABNORMALITY OF L-FUCOSE

[75] Inventors: Takeshi Sakai, Kusatsu; Hiroko Yokota, Otsu; Kazuki Yamamoto, Moriyama; Sadaji Yokoyama; Susumu Matsui, both of Otsu; Ikunoshin Kato; Akira Obayashi, both of Uji, all of Japan

[73] Assignee: Takara Shuzo Co., Ltd., Kyoto, Japan

[21] Appl. No.: 260,518

[22] Filed: Oct. 20, 1988

[30] Foreign Application Priority Data

Nov. 19, 1987 [JP] Japan .................. 62-290735
May 10, 1988 [JP] Japan .................. 63-111576

[51] Int. Cl.$^5$ .................. G01N 33/493; G01N 33/50
[52] U.S. Cl. .................. 436/64; 435/25; 436/93; 436/813
[58] Field of Search .................. 436/64, 93, 813; 73/23.1; 435/25

[56] References Cited

U.S. PATENT DOCUMENTS 4,338,811  7/1982  Miyagi et al. .................. 73/23.1

FOREIGN PATENT DOCUMENTS 0074996  4/1984  Japan .................. 435/25

OTHER PUBLICATIONS

Honda, S., Suzuki, S; Kakehi, K; "Analysis of the Monosaccharide Compositions of Total Non-Dialyzable Urinary Glycoconjugates by—the Dithioacetal method" J. of Chromatog, vol. 226, (1981) 341–350.

Petrini, M.; Azzarà, A.; Polidori, R.; Vatteroni, M. L.; Caracciolo, F.; "Serum Factors Inhibiting Some Leukocytic Functions in Hodgkin's Disease" Clinical Immunology and Immunopathology, vol. 23, pp. 124–132, (1982).

Willems P. J.; Darby J. K.; DiCioccio, R. A.; Nakashima, P.; Eng., C; Kretz, K. A.; Cavilli-Sfolza, L. L.; Shooter, E. M., O'Brien J. S., "Identification of a Mutation in the Structural α-L-Fucosidase Gene in Fucosidosis," Am J. Hum. Genet; 43:756–763, 1988.

Maler, T.; Duthie, M.; Alon, N.,; Riordan J. R.; "α-L-Fucosidase is Quantitatively Reduced in Cultured Lymphoblasts from Patients with Cystic Fibrosis", J. of Biol. Chem., vol. 256, No. 3, 2/10/81, pp. 1420–1427.

Waalkes, T. P.; Mrochek J. E.; Dinsmore, S. R.; Tormey, D. C., "Serum Protein–Bound Carbohydrates for Following the Course of Disease in Patients with Metastatic Caicinoma," Natl. Cancer, Inst., vol. 61, No. 3, Sep. 1978, pp. 703–707.

*Primary Examiner*—Christine M. Nucker
*Attorney, Agent, or Firm*—Wenderoth, Lind & Ponack

[57] ABSTRACT

A method is provided for the detection of a disease associated with the metabolic abnormality of L-fucose in a subject. The concentration of free L-fucose in a specimen from the subject is determined and the determined concentration is compared with a normal concentration of free L-fucose.

2 Claims, 2 Drawing Sheets

METHOD FOR THE DETECTION OF DISEASES ASSOCIATED WITH THE METABOLIC ABNORMALITY OF L-FUCOSE

This invention relates to a method for the detection of diseases associated with the metabolic abnormalities or disorder of L-fucose such as gastric ulcer, liver cirrhosis and carcinomas in humans.

Various forms of complex glycochains, i.e., glycoproteins and glycolipids, are present in the living body of higher animals. Most of these complex glycochains include, as their constituent, L-fucose. The complex glycochains containing L-fucose in the chain are represented by, for example, a mucous glycoprotein that protects the gastric mucosa, a mucous glycoprotein secreted from the submaxillary glands, $alpha_1$-acid glycoprotein and $beta_2$-glycoprotein synthesized and secreted by the liver, a glycoprotein on the surface of the erythrocytic membrane and gamma-globulin that is formed in the bone marrow, and the other glycoprotein and glycolipid present on the surface of the cellular membrane. As mentioned above, there are a wide variety of complex glycochains containing L-fucose in the living body. On the other hand, it has been known that the structure of the sugar chains in the complex glycochains containing L-fucose alters or that the amount of these glycochains in the body fluid changes in some diseases; the reported cases, for example, are the reduced secretion of mucous glycoprotein in gastric ulcer or cancer, reduced secretion of glycoproteins such as $alpha_1$-acid glycoprotein in liver cirrhosis and hepatoma, and changes in the sugar chain structure of glycoproteins and glycolipids on the cellular surface membrane resulting from carcinogenesis of the cells.

These reports, however, simply describe the changes in the structure of glycochains or the amount of glycochains, and fail to explain each of individual metabolic changes in the constituent saccharides of these glycochains in disease state. Moreover, there has been no report about the correlation between the metabolism of L-fucose and a specific disease.

It is an object of this invention to provide a novel method for the detection of specific diseases associated with L-fucose metabolic abnormalities by use of L-fucose as a marker.

This invention relates generally to a method for the detection of diseases associated with the metabolic abnormalities of L-fucose, which is characterized by the comparison of the free L-fucose concentration in specimen taken from subject with its normal value.

The diseases associated with the metabolic abnormalities of L-fucose are the following (1), (2) and (3).

(1) Diseases of visceral organs with relatively large quantity of L-fucose.
(2) Diseases of visceral organs that produce or secrete substances that contains relatively large quantity of L-fucose.
(3) Diseases that cause changes in the L-fucose quantity in complex glycochains on the cellular surface.

The above (1), (2) and (3) are described more particularly as follows: The examples of (1) are gastric ulcer or gastric cancer. The examples of (2) includes liver cirrhosis, hepatoma, breast cancer, myeloma. The examples of (3) represent lung cancer, rectal cancer and other cancers.

As a consequence of a series of studies, the inventors of this invention have confirmed that higher concentrations of free L-fucose are present in specimens taken from patients with gastric ulcer, gastric cancer, liver cirrhosis, hepatoma and other cancers than in those from healthy individuals and found that the free L-fucose concentration can be used as an index for diseases associated with the metabolic abnormalities of L-fucose.

The specimens usable in this invention are exemplified by urine, blood, etc.; the urine is preferable in that it is simple to collect and use.

In this invention, the methodologies for measuring free L-fucose in specimens are not restricted; for example, enzymatic methods and high performance liquid chromatography (hereafter called HPLC) are among them.

The enzymatic methods include those using L-fucose dehydrogenase (hereafter called FDH); as described in the Japanese Patent Kokai No. 175197/87, when FDH is used, one method determines the free L-fucose concentration from an absorbance of NADH at 340 nm and the other calculates it from an absorbance of formazan dye at a wavelength in the visible spectrum.

The FDH used in the quantitative analysis is, for example, one listed in the Japanese Patent Kokai No. 155085/87 or the other which is derived from porcine liver.

Moreover, when FDH is employed, it is preferable to pretreat specimens with bilirubin oxidase because this procedure reduces blank value.

Furthermore, the concentration of free L-fucose may be measured by HPLC; the quantitation by HPLC is performed by the use, for example, of commercially available instruments made by Shimadzu Seisakusho Co. and Dionex Corporation.

This invention is explained by reference to drawings and examples as follows: It is, however, our intention that this invention be not limited by any of the details of descripton of the following examples.

EXAMPLE 1

The concentrations of free L-fucose were measured using urine samples from 21 healthy individuals, 7 patients with gastric ulcer, 5 patients with liver cirrhosis, 35 patients with gastric cancer, 12 patients with hepatoma, 5 patients with lung cancer, 6 patients with breast cancer, 5 patients with rectum cancer and one patient with goiter. Free L-fucose was measured as follows:

| | |
|---|---|
| Urine | 0.1 ml |
| 1 unit/ml Bilirubin oxidase (Takara Shuzo Co. Ltd.), incubated at 37° C. for 15 min | 0.1 ml |
| 300 mM Glycine-sodium hydroxide-buffered solution (pH 8.2), containing 10 mM sodium azide | 0.25 ml |
| 2 mM Iodonitrotetrazolium | 0.15 ml |
| 0.1 mM 1-Methoxyphenazine methosulfate | 0.05 ml |
| 20 mM NAD+ | 0.05 ml |
| 70 units/ml FDH (Takara Shuzo Co., Ltd.), incubated at 37° C. for 15 min | 0.1 ml |

| -continued | |
|---|---|
| 0.2 M Hydrochloric acid | 2.0 ml |

Reactions were allowed to proceed by the above order, an absorbance was measured at 492 nm, and the reading was $OD_t$. At the same time, reactions were allowed to take place in the above reaction system using water instead of 70 units/ml of FDH to measure an absorbance at 492 nm; the reading was $OD_b$.

$$OD_t - OD_b = delta\text{-}OD$$

Figure 2:
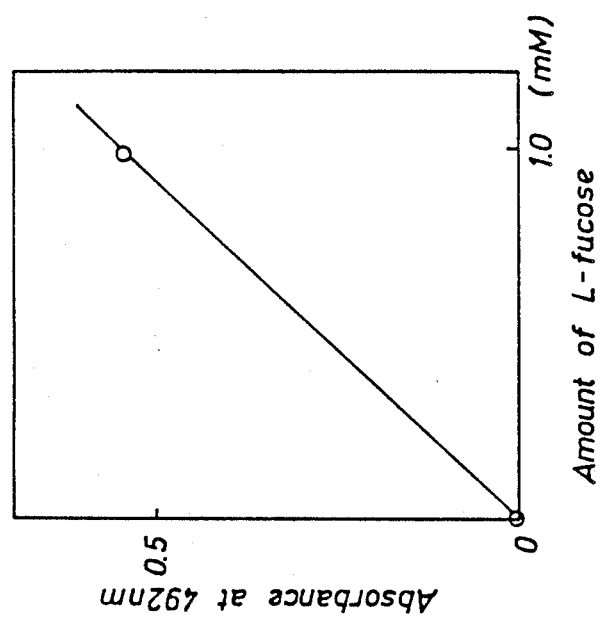
FIG. 2 is a graph of the calibration curve to measure the urinary concentration by the method in this invention.

When the concentration of free L-fucose was calculated from the delta-OD, reactions were allowed to proceed in the above reaction system using water and 1 mM L-fucose instead of urine, and an absorbance was measured at 492 nm in order to construct a graph of the calibration curve by plotting the absorbance at 492 nm on the axis of ordinate and the free L-fucose concentration on the axis of abscissa. The urinary concentration of L-fucose was calculated based on the calibration curve and delta-OD value. FIG. 2 shows the calibration curve (the axis of abscissa: L-fucose concentration (mM), and the axis of ordinate: absorbance at 492 nm)

Figure 1:
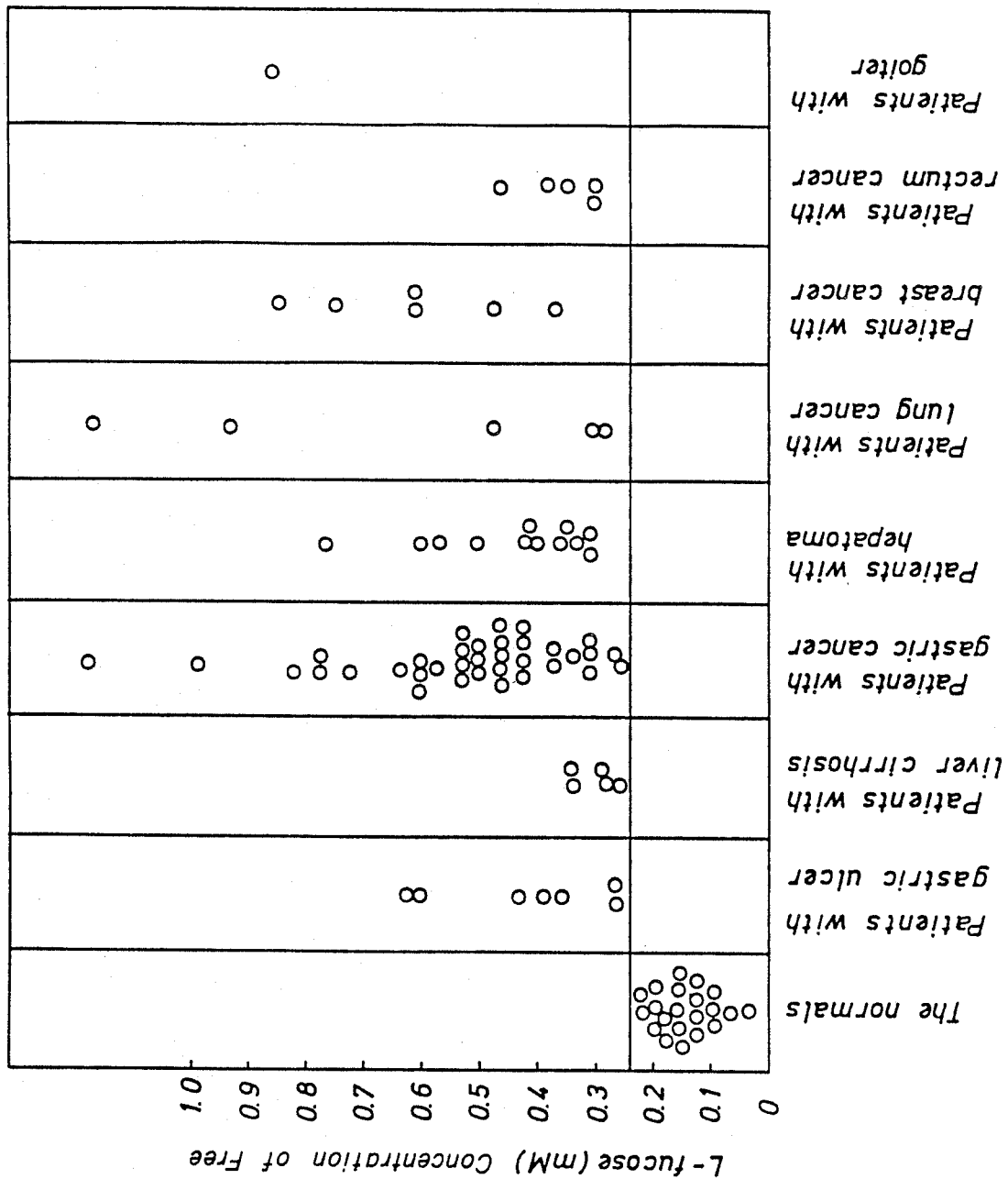
FIG. 1 is a graph constructed by plotting, by patient, the urinary concentration of free L-fucose measured by the method in this invention.

Assay results of urinary free L-fucose are given in FIG. 1; this figure is a graph, on which had been plotted the urinary free L-fucose concentrations by patient measured by this invention.

As shown in FIG. 1, there was a difference in the distribution of the urinary free L-fucose concentrations between healthy individuals and patients with gastric ulcer, liver cirrhosis, gastric cancer, hepatoma and other cancers; it was found that higher concentrations of urinary free L-fucose are present in patients with gastric ulcer, liver cirrhosis and a variety of cancers than in healthy individuals.

EXAMPLE 2

Quantitation of free L-fucose by HPLC:

When the concentrations of urinary free L-fucose were quantitatively measured under the following assay conditions, almost the same concentrations as those in Example 1 were obtained.

Assay conditions:
Column: Shim-pack CLC-NH$_2$ 6×150 mm (Shimadzu Seisakusho Co.)
Mobile phase: 75% Acetonitrile
Temperatrure: 30° C.
Detector: Reflactive index detector Shodex RI SE-51 (Showa Denko Co.)

As described above, this invention indicates that the urinary concentration of free L-fucose serves as a marker of diseases associated with the metabolic abnormalities of L-fucose such as gastric ulcer, liver cirrhosis, gastric cancer, hepatoma and other cancers; as a consequence, a novel method for the detection of the above diseases has been developed. In particular, this method enables the detection of gastric ulcer, gastric cancer, liver cirrhosis and hepatoma inexpensively and without any pain, thereby improving the rate of subject participation at mass screening.

What we claim is:

1. A method for the detection of a disease associated with the metabolic abnormality of L-fucose in a subject, which comprises determining the concentration of free L-fucose in a urine specimen from the subject, and comparing the determined concentration with a normal concentration of free L-fucose.

2. A method for the detection of gastric ulcer, liver cirrhosis or cancer in a human subject, which comprises determining the concentration of free L-fucose in a urine speciment from the subject and comparing the determined concentration with a normal concentration of free L-fucose.

* * * * *